United States Patent [19]

Grisoni et al.

[11] Patent Number: 5,611,968
[45] Date of Patent: Mar. 18, 1997

[54] METHOD OF MAKING INTRAOCULAR LENSES

[75] Inventors: Bernard F. Grisoni, Arlington, Tenn.; Glenn R. Sussman, Lake Forest, Calif.

[73] Assignee: Allergan, Waco, Tex.

[21] Appl. No.: 291,386

[22] Filed: Aug. 16, 1994

[51] Int. Cl.$^6$ ........................................................ B29D 11/00
[52] U.S. Cl. ........................... 264/2.1; 264/1.7; 264/2.4; 264/2.7; 264/310; 425/808
[58] Field of Search ..................... 264/2.1, 2.4, 2.6, 264/2.7, 310, 312, 1.7; 425/808, 402

[56] References Cited

U.S. PATENT DOCUMENTS

| | | | |
|---|---|---|---|
| 3,045,287 | 7/1962 | Yost et al. | 264/310 |
| 3,356,242 | 12/1967 | Cleereman | 264/310 |
| 3,632,841 | 1/1972 | Fortin . | |
| 3,907,952 | 9/1975 | Cleereman | 264/312 |
| 4,151,245 | 4/1979 | Suzuki | 425/446 |
| 4,288,478 | 9/1981 | Kinoshita et al. | 264/312 |
| 4,360,483 | 11/1982 | Ayres . | |
| 4,454,203 | 6/1984 | Franz et al. . | |
| 4,550,057 | 10/1985 | Kataoka . | |
| 4,614,629 | 9/1986 | Economy et al. | 264/310 |
| 4,687,485 | 8/1987 | Lim et al. . | |
| 4,725,397 | 2/1988 | Nakauchi et al. . | |
| 4,781,717 | 11/1988 | Grendahl . | |
| 4,813,954 | 3/1989 | Siepser . | |
| 4,834,750 | 5/1989 | Gupta . | |
| 4,932,968 | 6/1990 | Caldwell et al. . | |
| 4,986,939 | 1/1991 | Hoffmann | 264/1.7 |
| 5,120,120 | 6/1992 | Cohen . | |
| 5,169,569 | 12/1992 | Ingram et al. . | |
| 5,322,649 | 6/1994 | Rheinish et al. | 264/2.7 |

FOREIGN PATENT DOCUMENTS

| | | |
|---|---|---|
| 0438043 | 7/1991 | European Pat. Off. . |
| 0444951 | 9/1991 | European Pat. Off. . |
| 2673574 | 9/1992 | France . |
| 1074395 | 7/1967 | United Kingdom . |

*Primary Examiner*—Mathieu D. Vargot
*Attorney, Agent, or Firm*—Frank J. Uxa

[57] ABSTRACT

New intraocular lenses and methods for producing such lenses. In one embodiment, the intraocular lens includes an optic; and at least one fixation member, e.g., haptic, secured to and extending from the optic, the fixation member being made from a rotated item including a polymer, the rotated item being derived by placing an item having a thickness and the same chemical make-up as the rotated item between two surfaces so that the surfaces each contact the item and are separated by the thickness, and rotating at least a portion of one of the surfaces around an axis substantially parallel to the thickness, provided that the intraocular lens has increased tensile strength relative to a substantially identical intraocular lens made from the original item. Methods of making intraocular lenses are also included.

20 Claims, 1 Drawing Sheet

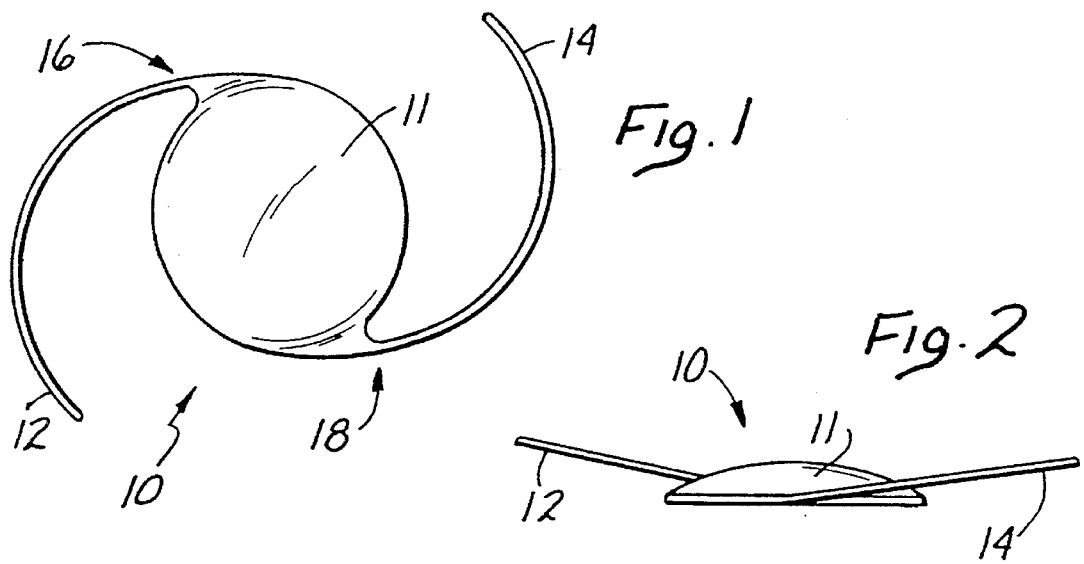
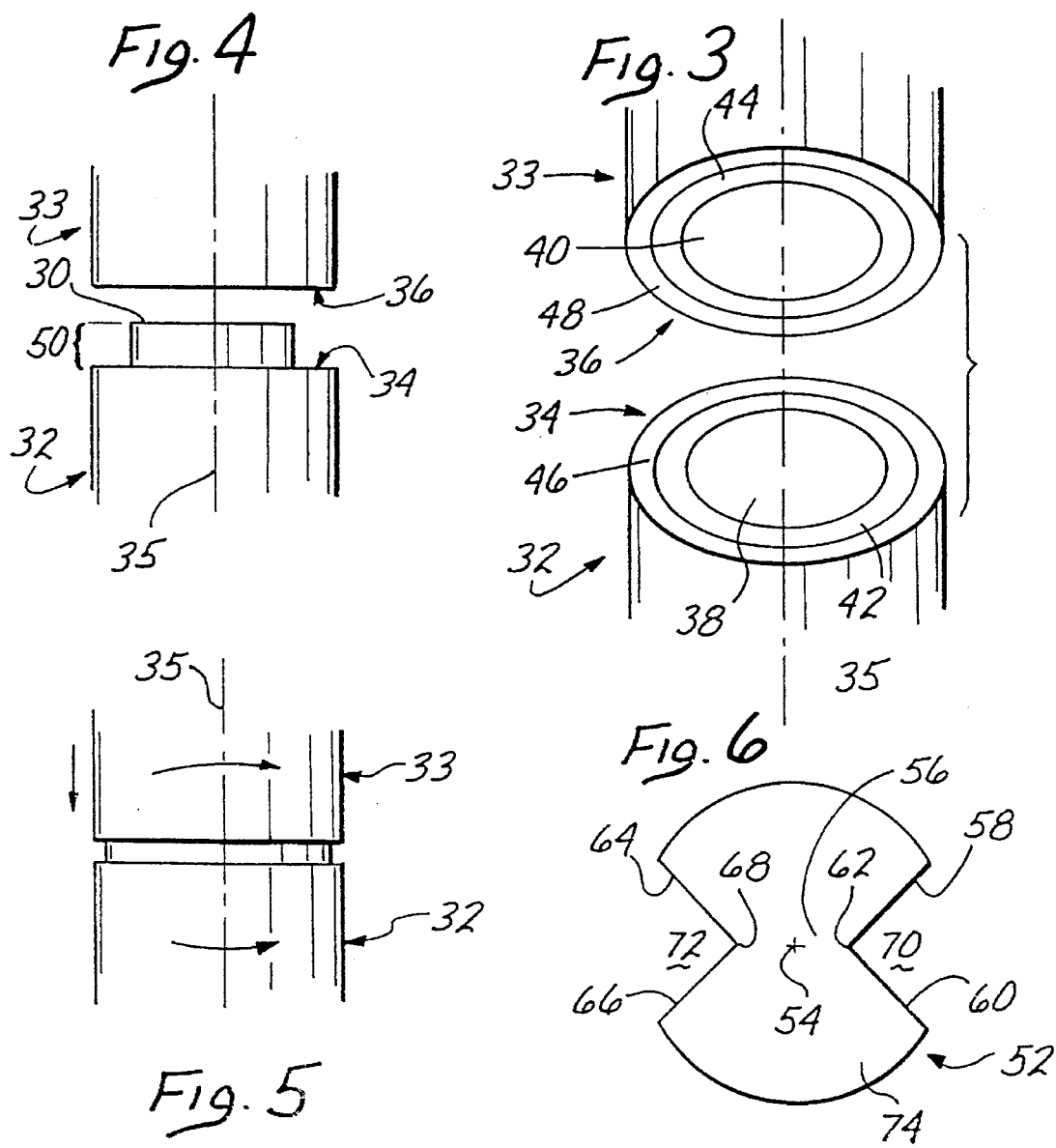

METHOD OF MAKING INTRAOCULAR LENSES

BACKGROUND OF THE INVENTION

The present invention relates to intraocular lenses and to methods for making such lenses. More particularly, the present invention relates to intraocular lenses having one or more enhanced physical properties, for example, tensile strength and/or flexibility and/or fatigue resistance, which benefit the lenses.

The use of intraocular lenses (IOLs) to improve vision and/or to replace damaged or diseased natural lenses in human eyes, particularly natural lenses impaired by cataracts, has achieved wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, preferably two, supporting structures, called fixation members or haptics, which are secured to and extend outwardly, in a generally curved direction, from the optic and are for contacting eye tissue to fix or hold the IOL in the proper position after implantation. The optic and the fixation member or members may each comprise a material such as a homopolymer of methyl methacrylate or polymethylmethacrylate (PMMA) or a copolymer containing methyl methacrylate or a polycarbonate or the like. The entire IOL, that is the optic and the fixation member or members, may be made of a single piece or item of material, for example, PMMA.

In order to obtain a high degree of performance, the IOL should be made of a material or materials which have good physical or mechanical properties. For example, the fixation member or members should have sufficient tensile strength, flexibility and fatigue resistance so as not to break or separate from the optic during IOL implantation and to be effective in long term use in the eye. Certain materials, in particular, the methyl methacrylate-containing polymers noted above, have certain properties, such as optic clarity and biocompatibility, which make them very useful in IOLs. However, it would be advantageous to enhance certain other physical properties, as noted above, of such materials to further benefit IOLs made at least in part from such materials.

European Patent Publication No. 0438043A2 discloses IOLs made from PMMA which is subjected to stretching along at least two mutually angulated axes to increase the materials' dimension along the axes of stretch by 20% to 65%, preferably by 40%, thereby providing increased tensile strength and flexibility. Several disadvantages are apparent with such a "multi-axial" stretching system. For example, the material may not be uniformly stretched, which can cause distortions and other irregularities in the material and the final IOL product. In addition, because a relatively complex and cumbersome clamping/stretching system is employed, a relatively high percentage of the stretched material must be discarded. Further, the amount or degree of stretching is quite high, apparently because of the relative inefficiency of the "multi-axial" stretching technique in providing improved mechanical properties. Materials which are highly stretched have a tendency to be more difficult, relative to unstretched materials, to manufacture, for example, machine, into IOLs.

Kataoka U.S. Pat. No. 4,550,057 discloses compressing PMMA sheets to reduce the thickness of the sheet by a factor of at least 3 and increase impact resistance by a factor of at least 10. Large compression forces and/or temperatures on the order of 130° C. to 160° C. are employed to achieve this large degree of compression. These compressed sheets are suitable as a glazing material for windows for vehicles and buildings. This patent does not in any way disclose or suggest anything about IOLs or making IOLs.

Fortin U.S. Pat. No. 3,632,841 discloses compression stretching large acrylic sheets at temperatures of 250° F. and above between polished, heated and lubricated plates to form compressed sheets which are about one-third as thick as the original sheets. This patent discloses that such compression stretching provides improved physical and optical properties. This patent does not in any way disclose or suggest anything about IOLs or making IOLs.

Franz et al U.S. Pat. No. 4,454,203 discloses coating an acrylic substrate with a compatible polymeric film which is less extensible than the substrate and pressing the coated article to reduce thickness so that the compressed article has a thickness of about one-third that of the original article. Reduced amounts of compressive force are apparently required to achieve this large reduction in thickness, and the resulting plastic article is said to have improved optical quality. This patent does not in any way disclose or suggest anything about IOLs or making IOLs.

There continues to be a need for IOLs having enhanced properties and for methods for making such IOLs.

SUMMARY OF THE INVENTION

New IOLs and methods for producing IOLs have been discovered. The present IOLs, which include an optic and at least one fixation member extending outwardly from the optic, are derived from materials, preferably containing methyl methacrylate-containing polymers, polycarbonates and the like, which have been subjected to controlled rotation, and preferably compression, between two surfaces to enhance one or more physical properties of the materials and the resulting IOLs. This rotation, and preferably the combination of rotation and compression, has been found to provide meaningful physical property enhancement. For example, the rotation and rotation/compression to which the materials are subjected in accordance with the present invention provides IOL fixation members having enhanced tensile strength and/or flexibility and/or fatigue resistance relative to IOL fixation members made from the unrotated material. The "rotated" material in accordance with the present invention may be further processed, for example, using conventional IOL manufacturing procedures, to obtain an IOL having advantageously enhanced physical properties. The present rotation and rotation/compression processing is particularly effective in providing IOLs which include fixation members or haptics having enhanced physical properties.

In one broad aspect, the present invention involves IOLs which comprise an optic and at least one fixation member which is secured to and extends outwardly, preferably in a generally curved direction, from the optic. The fixation member or members, and preferably the optic as well, are made from a rotated item comprising a polymer, preferably selected from methyl methacrylate homopolymers, methyl methacrylate-containing copolymers, polycarbonates and the like. The rotated item is derived by placing an item having a thickness and the same chemical make-up (chemical composition) as the rotated item between two surfaces so that the surfaces each contact the item and are separated by the thickness. At least a portion of one of the surfaces is rotated around an axis of rotation substantially parallel to the thickness. The tensile strength of the rotated item is increased relative to the tensile strength of the item prior to being rotated. Thus, the intraocular lens made from the rotated item has increased tensile strength relative to a substantially identical intraocular lens made from the original item. Preferably, the item is subjected to compression, more preferably during or substantially simultaneously with the above-noted rotation, along an axis substantially parallel to the thickness of the item to reduce the thickness. This compression provides a further physical property enhancement, particularly for the fixation member or members of the IOL. Since the rotation is preferably in the general direction that the fixation member or members extend away from the optic, the rotation or rotation/compression is particularly effective in enhancing the physical properties, for example, tensile strength and/or flexibility and/or fatigue resistance, of the fixation member or members, for example, at or in the area of the junction or junctions between the optic and the fixation member or members.

In one embodiment, the thickness of the item is reduced by about 50% or about 30% or less as a result of the compression. In other words, the compressed thickness of the compressed item is equal to about 50% or about 70% or more of the thickness of the original, unrotated and uncompressed item. The present invention is based, in part, on the discovery that sufficient enhancements in material physical properties can be achieved to benefit IOLs with a controlled amount of compression in combination with rotation, as described herein. An additional benefit of this controlled rotation/compression is that the rotated/compressed material is substantially free of distortions and non-uniformities which become more prevalent as the degree of compression or stretching to which an item is subjected is increased.

In a further embodiment, the item is preferably subjected to rotation or rotation/compression at a temperature in the range of about 80° C. to about 130° C. or about 150° C., more preferably about 80° C. to about 125° C. These relatively mild temperatures are consistent or in line with the controlled rotation or rotation/compression to which the item is subjected in accordance with the present invention. The mild temperatures noted herein reduce the amount of time involved in processing, for example, in heating and cooling, the material in accordance with the present invention. In addition, these mild temperatures reduce, or even eliminate, any distortions or non-uniformities which can result in processing the present materials at higher temperatures where the materials are more flowable and subject to change. Further, such mild temperatures reduce, or even eliminate, depolymerization of the present materials so that longer polymer chains are maintained and rotated materials having one or more superior physical properties are obtained, relative to processing at higher temperatures.

In one embodiment, only the fixation member or members of the IOL are produced from a rotated item in accordance with the present invention. Alternately, the optic and fixation member or members of the IOL are produced from the rotated item of material. Preferably, a single IOL is formed from the rotated item. However, it should be noted that at least the fixation members for two, three, four or more IOLs can be produced from a single rotated item.

In another aspect of the present invention, methods for making IOLs are provided. These methods comprise placing an item comprising a polymer and having a thickness between two surfaces so that the surfaces each contact the item and are separated by the thickness. At least a portion of one of these surfaces is rotated around an axis of rotation substantially parallel to the thickness to form a rotated item having increased tensile strength relative to the item. An IOL is formed from the rotated item and includes an optic and at least one fixation member secured or joined to the optic and extending outwardly, preferably in a generally curved direction, from the optic. In a particularly useful embodiment, the forming step includes machining the rotated item. Preferably, the present methods further comprise compressing, more preferably during or substantially simultaneously with the above-noted rotating, the item to reduce the thickness. The item comprises a polymer, preferably selected from methyl methacrylate homopolymers, methyl methacrylate-containing copolymers, polycarbonates and the like.

The present IOLs, and in particular the fixation members of each IOL, have enhanced physical properties which reduce the risk of disassembly or degradation during installation or long term use in the eye. Such physical property enhancement is achieved with little or no detriment, for example, to the overall IOL manufacturing process. Further, the present methods for producing IOLs involve controlled rotation, and preferably controlled rotation/compression, so as to reduce, and even minimize, material waste, energy and processing inefficiencies, and distortions and non-uniformities in the final IOL products. The present invention very efficiently and effectively provides IOLs which have advantageously enhanced physical properties and are useful and durable.

These and other aspects and advantages of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a front view of a typical IOL including optic and fixation members made of a material embodying principles of the present invention.

FIG. 2 is a side view of the lens of FIG. 1.

FIG. 3 is a front view of a portion of an apparatus useful in practicing the present invention.

FIG. 4 is a side view of the apparatus shown in FIG. 3 together with an item to be rotated and compressed.

FIG. 5 is a side view of the apparatus shown in FIG. 3 as the item is being rotated and compressed.

FIG. 6 is a top view of an item which is subjected to rotation prior to being formed into an IOL.

DETAILED DESCRIPTION OF THE INVENTION

Many different IOL configurations and sizes may be employed in the present invention. To illustrate, a typical IOL is shown generally at 10 in FIG. 1, and includes an optic 11 suitably shaped for proper focusing and having integrally formed fixation members or haptics 12 and 14 extending outwardly in a generally curved direction therefrom. IOL 10 may be plano-convex, as shown, or bi-convex, concavo-convex or any other optical configuration as desired. The optic may also have refractive and diffractive optic portions, several refractive curves or an aspheric surface to give bifocal or multifocal capabilities and be formed of a material having different optical or physical properties than the material forming haptics 12 and 14. Any haptic shape, configuration, or number may be utilized in accordance with the teachings of the present invention. Small apertures, notches and the like may be provided in the optic 11, for example, adjacent the connection with haptics 12 and 14, respectively, for reception of implantation tools.

In lenses of this type, the central portion or optic is a solid body, for example, about 5 mm to about 8 mm in diameter, with the very small cross section fixation members or haptics extending outwardly in a generally curved direction from the optic to create an overall size, between the free ends of the haptics, in the range of about 9 mm to about 14 mm. As illustrated in FIG. 1, the haptics 12 and 14 extend outwardly from the optic 11 in a generally curved direction rather than extending outwardly from the optic in a straight line direction. Any forces exerted on the haptics, for example, during installation or implantation of the IOL, or during use of the IOL, create high stress at the junctions 16 and 18 between the haptics 12 and 14, respectively and the optic 11 and along the curved length of the haptics. It is thus advantageous that the fixation member or members have high tensile strength, flexibility and fatigue resistance.

The items, for example, cores, buttons and the like, employed in accordance with the present invention comprise polymers, for example, polymers the molecules of which become more oriented or aligned upon the application of a force. Such polymers are preferably selected from methyl methacrylate homopolymers, co-polymers of methyl methacrylate and one or more other monomers, such as butyl acrylate, ethyl acrylate, lauryl acrylate and the like, polycarbonates and the like. In addition, the presently useful polymers can include polymerizable ultraviolet (UV) light absorbers, for example, present in the range of about 0.01% to about 2% by weight of the copolymer, effective to provide the desired degree of UV absorbance to the final IOL product. Examples of such UV absorbing monomers include functionalized benzophenones, functionalized benzotriazoles and the like. The presently useful items may include an effective amount of one or more other components to provide or enhance one or more properties which are beneficial in making the IOL and/or in the final IOL itself. For example, a UV absorbing additive (not polymerized) may be included or physically mixed into the item.

The polymer or polymers preferably comprise a major amount, i.e., at least about 50% by weight, and more preferably at least about 80% or about 90% by weight, of the item to be processed in accordance with the present invention. The optic of the final IOLs, and preferably the rotated items, are optically clear.

The following description focuses primarily on both rotating and compressing an item prior to forming the rotated item into an IOL. However, it should be understood that, while the combination of rotation and compression is preferred, substantially non-compressive rotation of the item provides substantial benefits, for example, IOLs with haptics which have enhanced tensile strength, flexibility and fatigue resistance, and is within the scope of the present invention.

In order to obtain a blank from which an IOL is to be formed in accordance with the present invention, an item, for example, a core of unrotated and uncompressed material, is provided. This item includes a polymeric material which is fully polymerized. Thus, the processing, e.g., rotating and compressing in accordance with the present invention, preferably results in substantially no additional polymerization or curing of this polymeric material.

Any suitable system and equipment may be employed to provide the rotated items and form IOLs from such rotated items in accordance with the present invention. Thus, the specific system and equipment employed is not critical and, for example, may be selected from systems and equipment which are conventionally employed to form IOLs from PMMA-type materials. The systems and equipment described herein are illustrative of the systems and equipment which may be employed.

In accordance with one embodiment, and with reference to FIGS. 3, 4 and 5, an uncompressed core 30, which is transparent and colorless and is made of, for example, PMMA, is placed on the first heating plate or platen 32 of a press or similar device suitable for applying a compressive force to the core. A second heating plate or platen 33 is aligned with the first heating plate 32 about axis 35 and is moved toward the first heating plate to apply compressive force on the core 30.

The heating plate surfaces, shown generally at 34 and 36, of first and second heating plates 32 and 33, respectively, include central portions 38 and 40, middle ring portions 42 and 44, and outer ring portions 46 and 48, respectively. Both central portions 38 and 40 do not rotate. Each of the middle and outer ring portions 42, 44, 46 and 48 is associated with a motor mechanism to rotate such surface portion in the direction shown around the central axis of the surfaces 34 and 36. This central axis is coincident with axis 35. Although each of these ring portions is adapted to rotate (or not to rotate) independently of each other, preferably each of the middle ring portions 42 and 44 rotates at the same speed in the same direction or only one of such ring portions rotate and each of the outer ring portions rotates at the same speed in the same direction or only one of such ring portions rotate. In one embodiment, the middle ring portions 42 and 44 rotate at one speed, and the outer ring portions 46 and 48 rotate at a faster speed. In another embodiment, the central portions 38 and 40 rotate at a speed which is slower than the speed at which the middle ring portions 42 and 44 rotate. Each ring portion which rotates preferably rotates in the same direction, for example, generally in the direction in which the haptics of the IOL extend outwardly away from the optic. Rotational speed may vary over a wide range, with rotation speeds in the range of about 0.01 revolutions per minute (rpm) to about 0.5 rpm preferably being employed.

Without wishing to limit the invention to any particular theory of operation, it is believed that the rotation and the combination of rotation and compression orients the polymeric material, for example, the macromolecules of the polymeric material, making up the item in the general direction at which the fixation member or members extend outwardly from the optic of the IOL produced from the rotated item. This directional orientation enhances the physical properties of the IOL, and in particular the fixation member or members of the IOL and the areas at or near the junctions between the fixation member or members and the optic of the IOL.

The heating plates are preferably sized so that the central portions of the plate surfaces have diameters which are within about 0.5 mm of the diameter of the optic to be produced from the rotated item. More preferably, such central portions have diameters which are smaller by about 0.5 mm or less than the diameter of the optic to be produced from the rotated item. The radial thicknesses of the middle and outer ring portions of the heating plate surfaces are preferably sufficient so that more than about 50%, more preferably more than about 80% and still more preferably substantially all, of the length of the fixation member or members to be produced from the rotated item are produced from those portions of the item that had been located between the middle ring portions and the outer ring portions (or those portions other than the central portions) of the heating plate surfaces.

The heating plates 32 and 33 are brought into contact with core 30 and are energized so as to heat the core to a temperature above about 30° C., preferably between about 80° C. to about 130° C. or about 150° C. and more preferably between about 80° C. to about 125° C. After the core 30 is heated to the desired temperature, the heating plates 32 and 33 are forced or urged toward each other while rotating as described above, thereby subjecting the core to rotation and compression along an axis substantially parallel to the thickness 50 of the core. This rotation/compression preferably results in reducing the thickness 50 of the core 30 by about 50% or about 30% or less, more preferably in the range of about 3% or about 5% to about 25% or 30%. After this rotation/compression the rotation of the plates is stopped and the rotated core is allowed to cool to below, for example, slightly below, the glass transition temperature of the core material before the compression force on the plates is released. The rotated core is typically cooled to room temperature, e.g., about 20° C. to about 25° C., before the compression force is released. The cooled, rotated core, which has an increased tensile strength relative to the original core 30, is now ready to be processed or formed into an IOL, such as IOL 10.

In one useful embodiment, only that portion or portions of the uncompressed material, for example, the uncompressed core 30, from which the haptic or haptics of the IOL are to be made are subjected to compression, as described herein. This can be accomplished by using heating plates designed to exert the desired rotational and compressive forces on the middle and outside rings of the core, while exerting little or no rotational and compressive forces on the central region of the core, from which the optic of the IOL is formed. Preferably, the compressive force is applied so that the core expands outwardly away from the central region and not inwardly toward the central region. One advantage of this embodiment is that the tensile strength and/or other physical property or properties of the haptic or haptics of the IOL are enhanced while the optic of the IOL is affected, for example, distorted, to a reduced extent, if at all, by the compressive force.

In the event the rotated core is to be produced substantially without the use of compressive forces, the original item (prior to rotation) preferably has a configuration which allows for changes in shape as a result of the application of rotation forces. One embodiment of such a configuration is illustrated by modified core 52 in FIG. 6. The central axis 54 of modified core 52 is surrounded by a solid central region 56. Modified core 52 includes first angled surfaces 58 and 60 which intersect at first junction 62, and second angled surfaces 64 and 66 which intersect at second junction 68. These angled surfaces form wedge-shaped spaces 70 and 72 into which the annuler region 74 of modified core 52 can expand upon the application of rotational forces.

Modified core 52 can be processed into a rotated core in a manner substantially analogous to that described with regard to core 30 except that substantially no compressive forces are applied to the modified core. Thus, the heating plates 30 and 32 are brought into contact with the modified core 52 to heat the modified core. After the desired heating has occurred, the middle and outer rings of the heating plates 30 and 32 are rotated to exert the desired rotational forces on the modified core 52. Throughout this rotation, and afterward until the modified core 52 is cooled, both of the heating plates 30 and 32 are maintained in contact with the modified core so that the central region 56 remains stationary during the rotation.

The rotated core, which is thicker and larger in all dimensions than the IOL to be made therefrom, may be processed in accordance with conventional IOL forming techniques to produce an integral IOL, such as IOL 10. To illustrate, the rotated PMMA core can be formed into a bi-convex single piece IOL by a process including the following steps:

(1) making a posterior cut on the rotated core;

(2) milling the rotated core;

(3) making an anterior cut on the rotated core; and (4) polishing and cleaning the processed core.

The final IOL can be wrapped, for example, individually wrapped, and stored prior to being used.

It has been found that the controlled rotation and rotation/compression employed in accordance with the present invention results in a rotated core which can be formed into an IOL, for example, using conventional IOL manufacturing techniques, such as those described herein, at least as effectively and efficiently as forming an IOL from the unrotated core using the same IOL manufacturing techniques.

The rotated materials processed as described herein provide IOLs with fixation members which have one or more enhanced properties, such as tensile strength, flexibility and fatigue resistance, for example, relative to IOLs including fixation members made from the unrotated material or the rotated material produced without compression as described herein.

While this invention has been described with respect to various specific examples and embodiments, it is to be understood that the invention is not limited thereto and that it can be variously practiced within the scope of the following claims.

What is claimed is:

1. A method of making an intraocular lens comprising:

placing an item comprising a polymer and having a thickness between two surfaces so that said surfaces each contact said item and are separated by said thickness, said polymer being selected from the group consisting of methyl methacrylate homopolymers, methyl methacrylate-containing copolymers and polycarbonates;

heating said item to a temperature of above about 30° C.;

rotating at least a portion of one of said surfaces around an axis of rotation substantially parallel to said thickness, provided that each of said surfaces includes a central portion which is not so rotated, to form a rotated item having increased tensile strength relative to said item; and forming an intraocular lens including an optic and at least one fixation member secured to said optic and extending from said optic from said rotated item.

2. The method of claim 1 wherein said intraocular lens is the only intraocular lens formed from said rotated item.

3. The method of claim 1 wherein said heating of said item is to a temperature in the range of about 80° C. to about 150° C.

4. The method of claim 1 wherein a single intraocular lens is formed from said rotated item.

5. The method of claim 1 which further comprises compressing said item along an axis substantially parallel to said thickness at conditions effective to reduce said thickness.

6. The method of claim 5 wherein said rotating and said compressing occur substantially simultaneously.

7. The method of claim 1 wherein at least a portion of one of said surfaces is rotated in the general direction that said at least one fixation member extends away from said optic.

8. The method of claim 1 wherein at least portions of both of said surfaces rotate in the same direction.

9. The method of claim 1 wherein said surface at least a portion of which is rotated comprises a plurality of surface portions each of which is rotated at a different speed.

10. The method of claim 1 wherein portions of each of said surfaces are rotated.

11. The method of claim 1 wherein said forming provides an intraocular lens including said optic and two of said fixation members from said rotated item.

12. A method of making an intraocular lens comprising:

placing an item comprising a polymer and having a thickness between two surfaces so that said surfaces each contact said item and are separated by said thickness;

heating said item to a temperature above about 30° C.;

compressing said item along an axis substantially parallel to said thickness at conditions effective to reduce said thickness;

rotating at least a portion of one of said surfaces around an axis of rotation substantially parallel to said thickness, provided that each of said surfaces includes a central portion which is not so rotated, to form a rotated item having increased tensile strength relative to said item; and, thereafter, forming an intraocular lens including an optic and at least one fixation member secured to said optic and extending from said optic from said rotated item.

13. The method of claim 12 wherein said intraocular lens is the only intraocular lens formed from said rotated item.

14. The method of claim 12 wherein said polymer is selected from the group consisting of methyl methacrylate homopolymers, methyl methacrylate-containing copolymers and polycarbonates.

15. The method of claim 12 wherein a single intraocular lens is formed from said rotated item.

16. The method of claim 12 wherein said rotating and said compressing occur substantially simultaneously.

17. The method of claim 12 wherein at least a portion of one of said surfaces is rotated in the general direction that said at least one fixation member extends away from said optic.

18. The method of claim 12 wherein at least portions of both of said surfaces rotate in the same direction.

19. The method of claim 12 wherein said surface at least a portion of which is rotated comprises a plurality of surface portions each of which is rotated at a different speed.

20. The method of claim 12 wherein said forming provides an intraocular lens including said optic and two of said fixation members from said rotated item.

* * * * *